(12) United States Patent
Torigoe et al.

(10) Patent No.: US 8,287,186 B2
(45) Date of Patent: Oct. 16, 2012

(54) SPECIMEN COLLECTING METHOD AND BLADE TEMPERATURE ESTIMATING METHOD

(75) Inventors: Taiji Torigoe, Hyogo (JP); Masahiro Yamada, Hyogo (JP); Ikuo Okada, Hyogo (JP); Toshio Sakon, Hyogo (JP); Hidetaka Oguma, Hyogo (JP); Takeshi Naito, Hyogo (JP); Koji Takahashi, Hyogo (JP); Soji Kasumi, Hyogo (JP); Keizo Tsukagoshi, Hyogo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 450 days.

(21) Appl. No.: 12/526,213

(22) PCT Filed: Jan. 30, 2008

(86) PCT No.: PCT/JP2008/051431
§ 371 (c)(1),
(2), (4) Date: Aug. 26, 2009

(87) PCT Pub. No.: WO2008/099676
PCT Pub. Date: Aug. 21, 2008

(65) Prior Publication Data
US 2010/0215148 A1 Aug. 26, 2010

(30) Foreign Application Priority Data
Feb. 16, 2007 (JP) .................................. 2007-036905

(51) Int. Cl.
*G01K 11/00* (2006.01)

(52) U.S. Cl. ........................................................ 374/159
(58) Field of Classification Search ................... 374/159
See application file for complete search history.

(56) References Cited

U.S. PATENT DOCUMENTS

| 7,311,481 | B2 * | 12/2007 | Kammermeier et al. | 409/137 |
| 2006/0186336 | A1 * | 8/2006 | Giannuzzi et al. | 250/307 |
| 2008/0069651 | A1 * | 3/2008 | Kammermeier et al. | 407/54 |

FOREIGN PATENT DOCUMENTS

| JP | 9-218139 A | | 8/1997 |
| JP | 09218139 A | * | 8/1997 |
| JP | 10-96684 A | | 4/1998 |
| JP | 2000-266644 A | | 9/2000 |

(Continued)

OTHER PUBLICATIONS

International Search Report of PCT/JP2008/051431, mailing date of Apr. 22, 2008.

*Primary Examiner* — Lisa Caputo
*Assistant Examiner* — Jamel Williams
(74) *Attorney, Agent, or Firm* — Westerman, Hattori, Daniels & Adrian, LLP

(57) ABSTRACT

In a specimen collecting method according to the present invention, a specimen is collected from a surface (114a) of a blade. An ultrasonic cutter having a cylindrical cutting blade is fed from the surface (114a) of the blade to a surface (110a) of a base material (100), and thus, a cylindrical incision is formed. After performing cutting to expand the incision outwardly, a rotating cutter (220) having a disc-shaped cutting blade (222) performs cutting inwardly from the cylindrical incision. Thus, a part (20a) situated inside the incision is cut away. The part (20a) becomes the specimen.

5 Claims, 12 Drawing Sheets

FOREIGN PATENT DOCUMENTS

| | | | | |
|---|---|---|---|---|
| JP | 2000266644 A | * | 9/2000 | |
| JP | 2002-277383 A | | 9/2002 | |
| JP | 2003-4548 A | | 1/2003 | |
| JP | 2003-4549 A | | 1/2003 | |
| JP | 2003004548 A | * | 1/2003 | |
| JP | 2003004549 A | * | 1/2003 | |
| JP | 2006-234816 A | | 9/2006 | |
| JP | 2006234816 A | * | 9/2006 | |

* cited by examiner

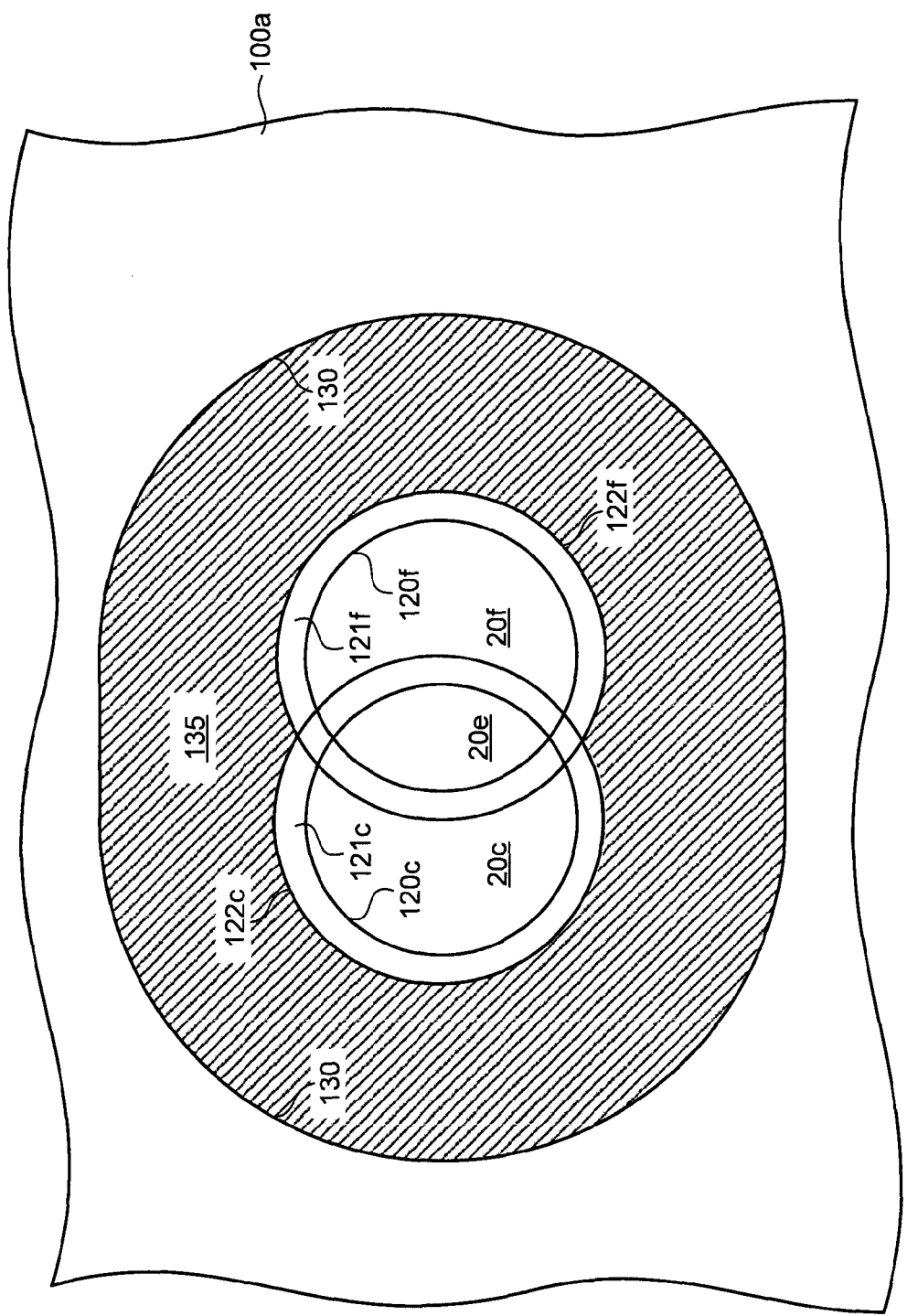

SPECIMEN COLLECTING METHOD AND BLADE TEMPERATURE ESTIMATING METHOD

TECHNICAL FIELD

The present invention relates to a specimen collecting method for collecting a specimen from a member provided with a layer on a surface thereof, and more particularly, to a specimen collecting method for collecting a specimen from a surface of a blade used for a gas turbine and to a blade temperature estimating method.

BACKGROUND ART

An approach for providing thermal barrier coating on a surface of a base material of a component is known to improve heat resistance of the base material. For example, in a gas turbine, an approach for providing thermal barrier coating on surfaces of a rotor blade and a stationary blade that are included in the turbine is known.

A member formed on a surface of a component by thermal barrier coating (hereinafter, "thermal barrier coat") is generally composed of two layers: an external layer called a top coat, and a layer called a bond coat that joins the top coat and the base material together. In a thermal barrier coat for a gas turbine, a ceramic having low thermal conductivity is used as the top coat, and an alloy having excellent oxidation resistance is used as the bond coat.

When the thermal barrier coat is exposed to a high temperature for a long time, a thermally grown oxide (hereinafter, "oxide scale layer") oxidized by the heat from the top coat, may be generated on the side of the bond coat facing the top coat. The oxide scale layer is generated on an area of the bond coat in contact with the top coat, and expands as thermal load applied to the thermal barrier coat increases. As the oxide scale layer expands and the thickness thereof increases, the oxide scale layer pushes up the top coat to, for example, form a crack on the top coat. As a result, the top coat may be separated from the base material and the bond coat.

To detect the separation of the thermal barrier coat in advance, an approach for estimating deterioration of the thermal barrier coat, that is, the degree of damage onto the barrier coat, is called for. In a technology disclosed in Patent Document 1, an impact force is applied to a thermal barrier coat. For example, a spherical object is collided thereagainst. Thus, the thermal barrier coat is destroyed, and information about deterioration of the thermal barrier coat can be obtained according to the condition of damage, such as the separation, provided thereto.

Patent Document 1: Japanese Patent Application Laid-open No. 2002-277383

DISCLOSURE OF INVENTION

Problem to be Solved by the Invention

In the technology disclosed in Patent Document 1, a strong impact force is applied to the thermal barrier coat and thus, structure thereof is destroyed. Therefore, the technology disclosed therein is not suitable for optically observing the thermal barrier coat and obtaining information about deterioration thereof.

The oxide scale layer is very thin, that is, the thickness thereof is 20 micrometers at most, and is not an oxide having a simple composition. Therefore, it is difficult to obtain information about condition of the oxide scale layer of the thermal barrier coating with a nondestructive approach.

More specifically, when deterioration of a blade thermal barrier coat provided on a blade of a gas turbine is evaluated, for example, the blade is cut away from the gas turbine, and thus, the thermal barrier coat is destroyed along with the components provided on the blade. Accordingly, each time the thermal barrier coat is evaluated, new components are required to be mounted on the blade in place of the destroyed components.

In view of the foregoing, it is an object of the present invention to provide a specimen collecting method that makes it possible to collect a specimen from a surface of a member without damaging the member and a blade temperature estimating method that makes it possible to estimate a temperature of a blade of a gas turbine without destroying the blade.

Means for Solving Problem

According to an aspect of the present invention, a specimen collecting method of collecting a specimen from a member whose surface is provided with a layer, includes: an incision forming step of forming a cylindrical incision by feeding a cylindrical cutter having a cylindrical cutting blade from the surface in the direction of thickness of the member to perform cutting; and a specimen cutting away step of cutting away a specimen formed inside the incision by inwardly cutting the member from the cylindrical incision.

Advantageously, the specimen collecting method further includes an incision expanding step of cutting the member so that the incision is outwardly expanded after forming the cylindrical incision. A rotating cutter having a disc-shaped cutting blade is inserted to the cylindrical incision to cut the member at the specimen cutting away step.

Advantageously, in the specimen collecting method, the member is a blade of a gas turbine, a surface of the blade is formed by providing a layer of a thermal barrier coat on a base material, the cylindrical cutter is fed until the cylindrical cutter comes in contact with the base material at the incision forming step, and the rotating cutter cuts the base material at the specimen cutting away step.

Advantageously, in the specimen collecting method, a plurality of incisions is formed so that the incisions partially overlap at the incision forming step.

According to another aspect of the present invention, a temperature estimating method of a blade in which a bond coat and a top coat are sequentially formed on a base material uses a specimen obtained by the specimen collecting method described above. A relationship between a thickness and a temperature of an oxide scale layer of the blade, and time is obtained based on a test piece having a same composition as the blade, and then, by utilizing the relationship, a metal temperature of the blade is estimated based on the thickness of the oxide scale layer of the specimen obtained from the gas turbine.

According to another aspect of the present invention, a temperature estimating method of a blade formed with a top coat that is a ceramic layer on a base material uses a specimen obtained by the specimen collecting method described above. An amount of a monoclinic crystal formed on the top coat of the obtained specimen is measured by X-ray diffraction method, and a surface temperature of the top coat is estimated based on the amount of the monoclinic crystal.

Effect of the Invention

The specimen collecting method according to the present invention includes an incision forming step of forming a cylindrical incision by using a cylindrical cutter having a cylindrical cutting blade and a specimen collecting method of cutting away a specimen by cutting a member inwardly from the cylindrical incision. Therefore, when the specimen is collected from the member, the specimen can be obtained from the surface thereof by applying thereto as less impact force as possible. Thus, accurate optical observation of the member can be implemented.

The specimen collecting method according to the present invention may further include an incision expanding step of cutting the member so that the incision is expanded outwardly after the cylindrical incision is formed on the member. Therefore, even if the difference between the inner diameter and the external diameter of the cylindrical cutter is small, and thus, the distance between the inner edge and the outer edge of the incision is also small, the rotating cutter can be inserted into the member so that an angle formed between the rotating cutter and the surface of the member is as acute as possible. As a result, the specimen cut away from the member can be as thin as possible. Therefore, a depression formed on the member after the specimen is cut away therefrom can be as shallow as possible.

In the specimen collecting method according to the present invention, the member is a blade of a gas turbine. The surface of the blade is configured so that a thermal barrier coat layer is formed thereon. At the incision forming step, the cylindrical cutter is fed into the blade until the cylindrical cutter comes in contact with the base material. At the specimen cutting away step, the rotating cutter cuts the base material. Thus, a specimen of a thermal barrier coat of a blade of a gas turbine can be collected with a small damage applied to the specimen. Therefore, without replacing the blade of the gas turbine after destroying the blade, an oxide scale layer can be evaluated to evaluate the deterioration of the blade.

In the specimen collecting method according to the present invention, a plurality of cylindrical incisions is formed so that the cylindrical incisions overlap partially. Therefore, a ratio between a total surface of specimens thus obtained and a surface of an area expanded outwardly from the incisions can be smaller than the case where only a single incision is formed. Accordingly, while minimizing a cumbersome step of expanding the incisions, a plurality of specimen can be obtained.

In the blade temperature estimating method according to the present invention, a relationship between a width and a temperature of the oxide scale layer of the blade, and time is first obtained based on a test piece having the composition similar to the composition of the blade. Thereafter, based on the relationship, the temperature of the blade can be estimated according to the thickness of the oxide scale layer of the specimen obtained from the gas turbine. Thus, while minimizing the damage applied to the blade, a temperature of the blade can be estimated. As a result, it is not necessary to replace the blade to obtain a specimen, and thus, deterioration of the blade can be evaluated at low cost.

In the blade temperature estimating method according to the present invention, a specimen is obtained with the specimen collecting method, and an amount of a monoclinic crystal generated on the top coat is measured with an X-ray diffraction method. Then, a temperature of the surface of the top coat is estimated based on the amount of the monoclinic crystal. Therefore, a temperature of the blade can be estimated while minimizing damage applied to the blade. As a result, it is not necessary to replace the blade to obtain a specimen, and thus, deterioration of the blade can be evaluated at low cost.

BRIEF DESCRIPTION OF DRAWINGS

FIG. 7 is a schematic of another example of the incision formed on the blade with the ultrasonic cutter.

EXPLANATIONS OF LETTERS OR NUMERALS

Figure 1:
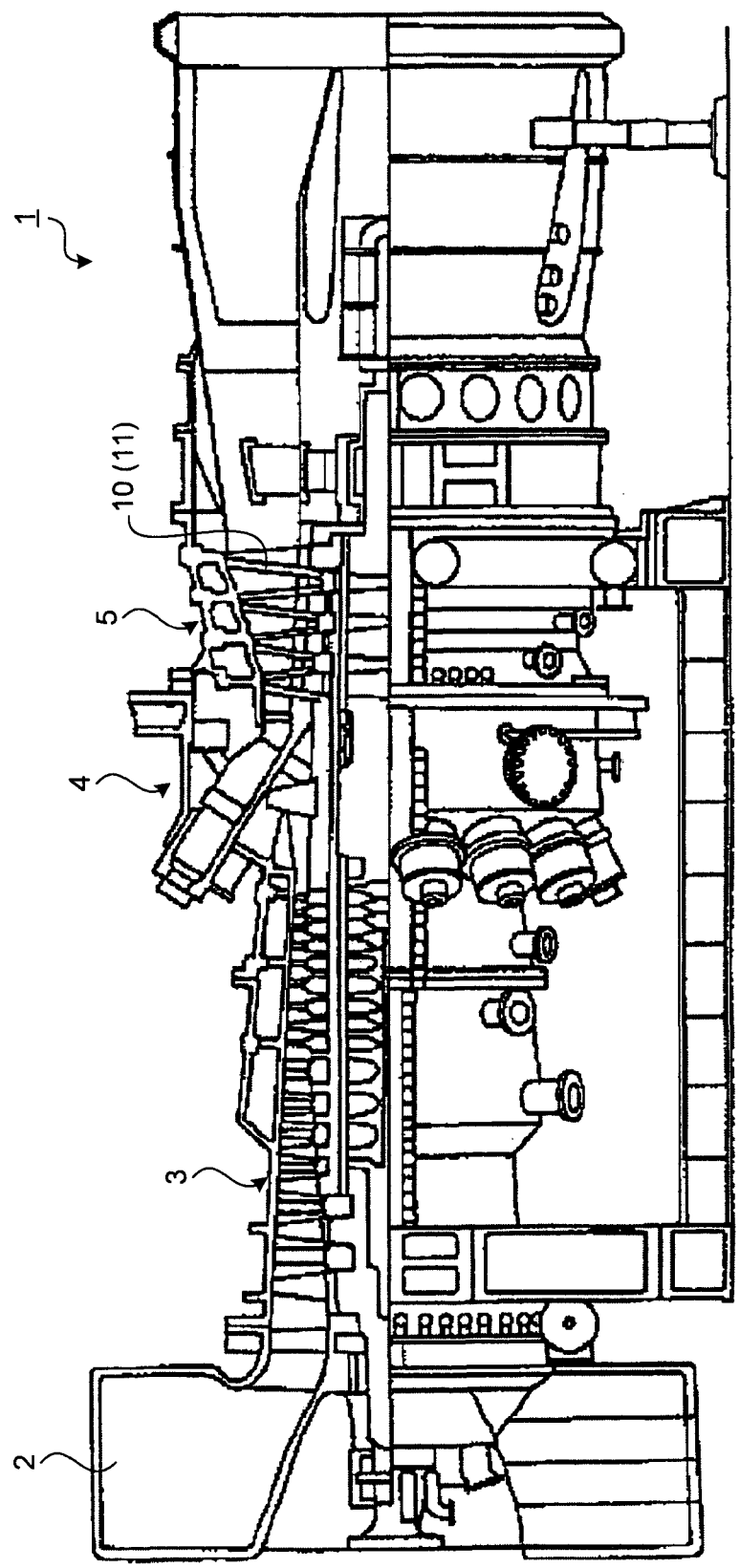
FIG. 1 is longitudinal sectional view of an overall configuration of a gas turbine according to a first embodiment of the present invention.

1 gas turbine
3 compressor
5 turbine
10 stationary blade (blade)
11 rotor blade (blade)
20 specimen
20*c* specimen
20*e* specimen 20f specimen
100 base material
100a base material surface
110 thermal barrier coat
112 bond coat
112s oxide scale layer
114 top coat
114a surface (blade surface)
120 inner edge
121 incision
122 outer edge
200 ultrasonic cutter (cylindrical cutter)
202 cutting blade (cylindrical cutting blade)
220 rotating cutter
222 cutting blade (disc-shaped cutting blade)
300 discharge wire cutting device (discharge sampling device)
310 electrode
315 electrode holder
320 sliding mechanism
330 rotating shaft
340 roller

BEST MODE(S) FOR CARRYING OUT THE INVENTION

Exemplary embodiments according to the present invention are described below in detail with reference to the accompanying drawings. The present invention is not, however, limited thereto. The elements described in embodiments below include various modifications that will readily occur to those skilled in the art or modifications substantially similar thereto.

First Embodiment

Figure 2:
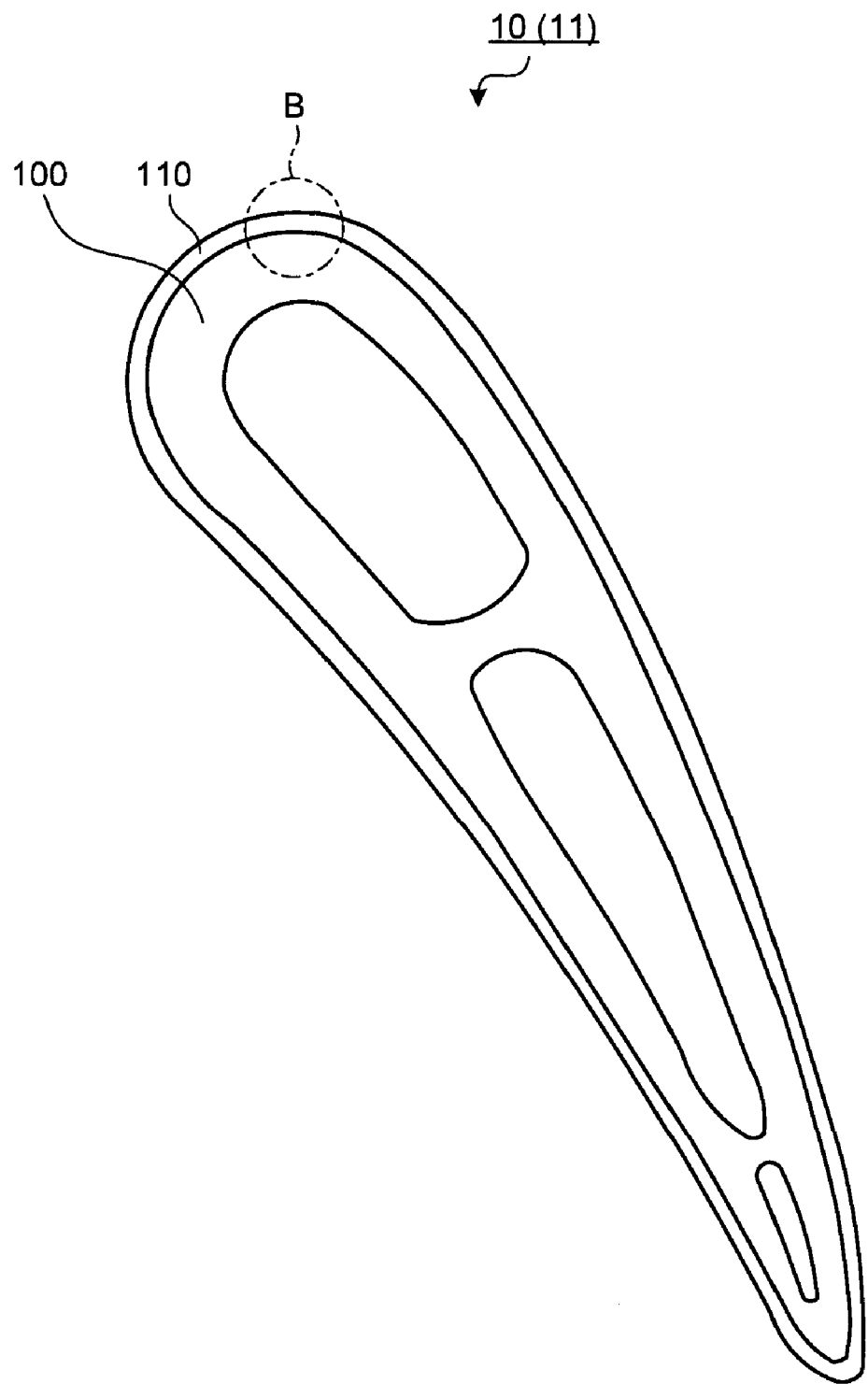
FIG. 2 is a sectional view of a blade according to the first embodiment.
Figure 3A:
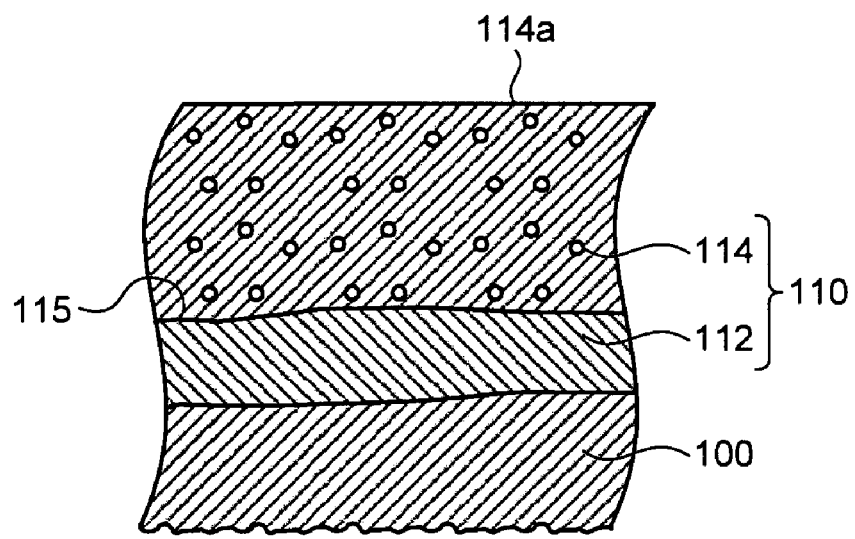
FIG. 3A is a schematic of an example of a thermal barrier coat provided on the blade according to the first embodiment.
Figure 3B:
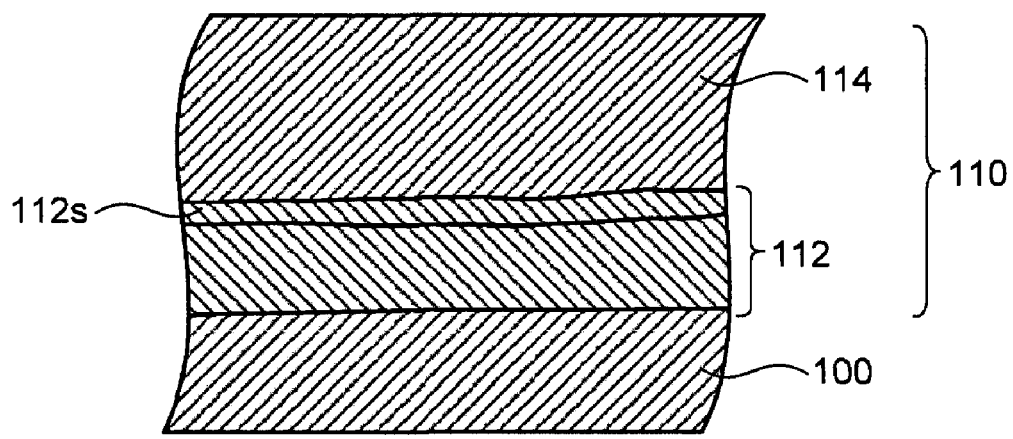
FIG. 3B is a schematic of a state of the thermal barrier coat when an oxide scale portion is generated within the thermal barrier coat according to the first embodiment.

A gas turbine and a thermal barrier coat provided on a blade of the turbine to which a collecting method of a thermal barrier coat specimen according to a first embodiment of the present invention is applied are described below in detail with reference to FIGS. 1 to 3B. FIG. 1 is a longitudinal sectional view of an overall configuration of the gas turbine. FIG. 2 is a sectional view of the blade. FIG. 3A is a schematic of an example of a thermal barrier coat provided on the blade, and FIG. 3B is a schematic of a state of the blade when an oxide scale layer is formed within the thermal barrier coat. Only substantial parts related to the present invention are schematically shown in FIGS. 1 and 2. FIGS. 3A and 3B are enlarged views of an area surrounded by a chain double-dashed line B shown in FIG. 2.

As shown in FIG. 1, an industrial gas turbine 1 according to the present embodiment includes an air intake 2, a compressor 3, a combustor 4, and a turbine 5, which are arranged in the described order from the upstream side to the downstream side in the air flow direction. Air taken into the gas turbine through the air intake 2 is compressed by the compressor 3 to produce compressed air that is at high temperature and high pressure. The compressed air is supplied to the combustor 4. The combustor 4 supplies the compressed air with gas fuel such as natural gas or liquid fuel such as diesel oil and heavy oil, and then, burns the fuel to produce combustion gas that is at high temperature and high pressure. The high temperature and high pressure combustion gas generated at the combustor 4 is supplied to the turbine 5.

In the turbine 5, stationary blades 10 and rotor blades 11 are alternately arranged. The turbine 5 converts energy of the combustion gas supplied from the combustor 4 into rotary torque through the stationary blades 10 and the rotor blades 11. A part of mechanical power received from the combustion gas by the turbine 5 is used to drive the compressor 3, and the rest of the mechanical power is used for purposes such as generating electric power. Here, the "blade" means a rotor blade or a stationary blade.

As shown in FIG. 2, the blades 10 (11) are configured so that all around the cross section of each of the blades 10 (11), a layer of thermal barrier coat 110 is provided on a surface 100a of a base material 100. The thermal barrier coat 110 is provided on the surface 100a of the base material 100 by performing vapor deposition or thermal spraying on the surface 100a. Because the thermal barrier coat 110 is provided on the blades 10 (11), a temperature (metal temperature) of the base material 100 can be lower than a temperature (for example, at 1500 degrees centigrade) of the combustion gas contacting the blades 10 (11).

As shown in FIG. 3A, the thermal barrier coat 110 according to the present embodiment includes a top coat 114 that is an external layer constituting an outer surface of each of the blades 10 (11) and a bond coat 112 that is a metal bonding layer bonding the top coat 114 and the base material 100 together. MCrAlY alloy (M: Ni, Co, Fe, or other metals) that is excellent in oxidation resistance is used as a material for the bond coat 112. The alloy is applied to the base material 100 by performing low pressure plasma spraying, and thus, the bond coat 112 is formed thereon. On the other hand, zirconium ceramic is used as a material for the top coat 114. The ceramic is applied to the bond coat 112 by performing air plasma spray or electron beam physical vapor deposition, and thus, the top coat 114 is formed thereon.

The top coat 114 is provided with a heat shielding property by, for example, having a plurality of pores formed at the interior thereof. The top coat 114 reduces a temperature of the base material 100 so that the temperature is lower than a temperature of the combustion gas contacting a surface 114a of the base material 100. The bond coat 112 bonds the top coat 114 and the base material 100 together, and prevents the base material 100 from oxidizing due to the combustion gas and heat thereof entering into the top coat 114. The surface 114a of the top coat 114 is the surface of each of the blades 10 (11).

When the gas turbine 1 configured as described above is in operation for a long time, in the thermal barrier coat 110 of each of the rotor blades 11 and the stationary blades 10, an oxide scale layer 112s that is a oxide is generated as shown in FIG. 3B on the area in the bond coat 112 that is at the boundary between the bond coat 112 and the top coat 114 as shown in FIG. 3B. An area of the oxide scale layer 112s expands (grows) as thermal load applied thereto increases. Thus, the top coat 114 is pushed up in the direction away from the base material 100. Thus, a crack may be formed in the top coat 114, or sometimes the top coat 114 may be separated from the base material 100.

Figure 4:
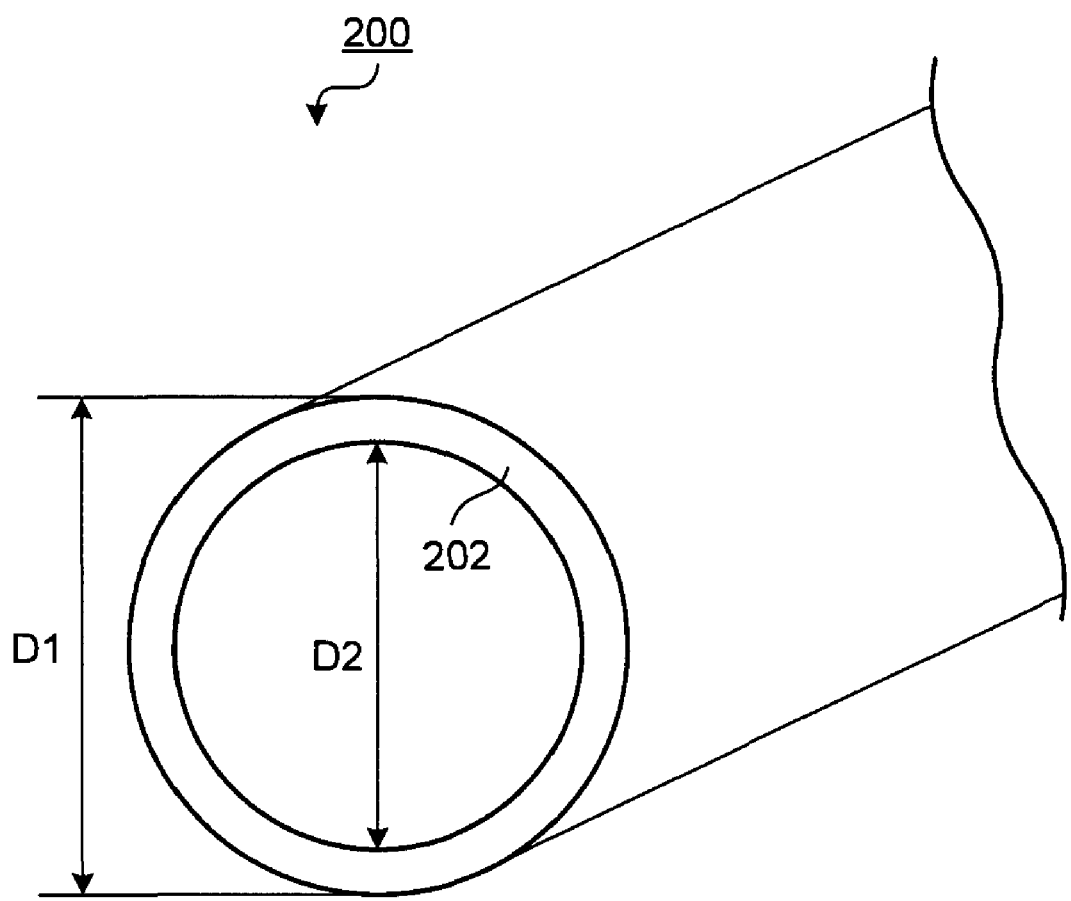
FIG. 4 is a perspective view of a cylindrical cutting blade of an ultrasonic cutter according to the first embodiment.

In the present embodiment, an ultrasonic cutter having a cylindrical cutting blade (cutting unit) is employed to collect a specimen of the thermal barrier coat from the surface of a blade of the gas turbine to obtain information about a status of generation of the oxide scale layer 112s in the thermal barrier coat 110. A method for collecting a specimen of the thermal barrier coat is described below in detail with reference to FIGS. 4 to 7. FIG. 4 is a perspective view of the cylindrical cutting blade of the ultrasonic cutter. FIGS. 5A to 5E are schematics for explaining the processes in each step of collecting the specimen. FIG. 6 is a top view of the thermal barrier coat while the specimen is collected. FIG. 7 is a schematic of another example of the incision formed on the blade with the ultrasonic cutter.

Figure 5A:
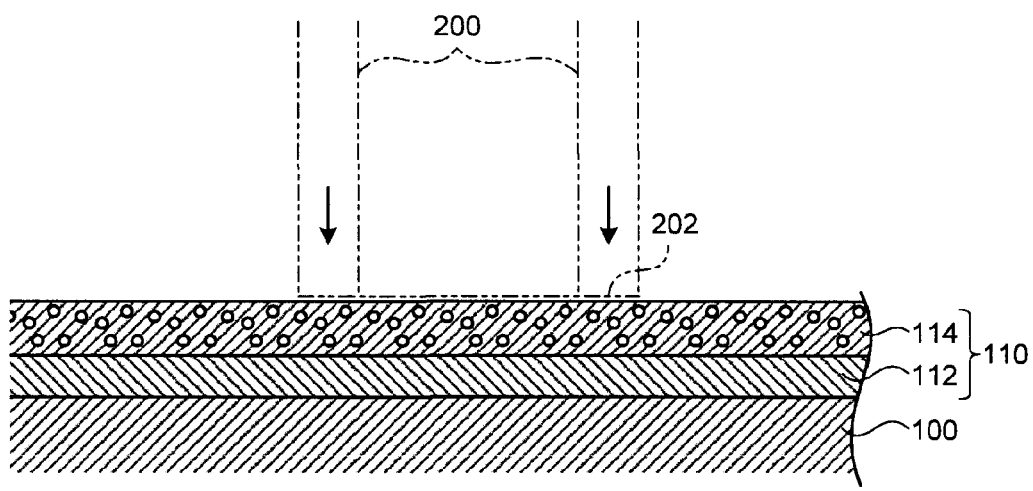
FIG. 5A is a schematic for explaining a process in each step of collecting a specimen according to the first embodiment, in which a state of the blade before being processed is shown.
Figure 5B:
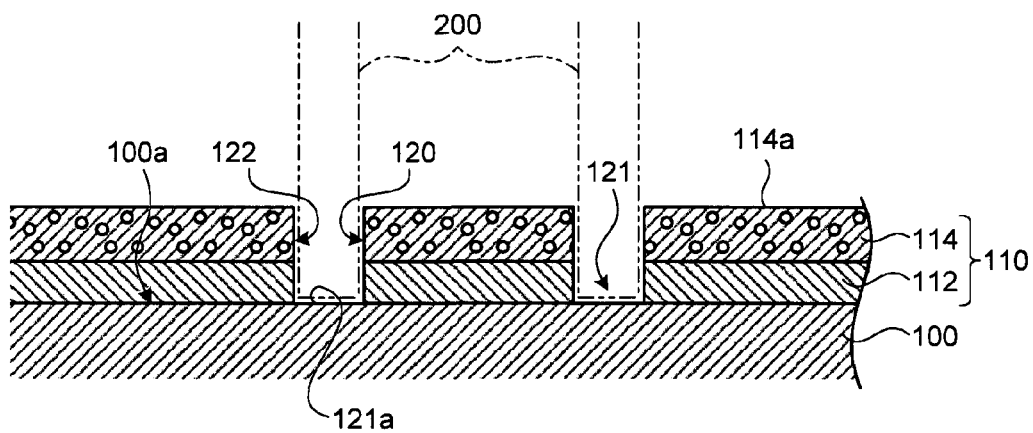
FIG. 5B is a schematic for explaining a process in each step of collecting a specimen according to the first embodiment, in which a state of the blade when a cylindrical incision is formed in the thermal barrier coat is shown.
Figure 5C:
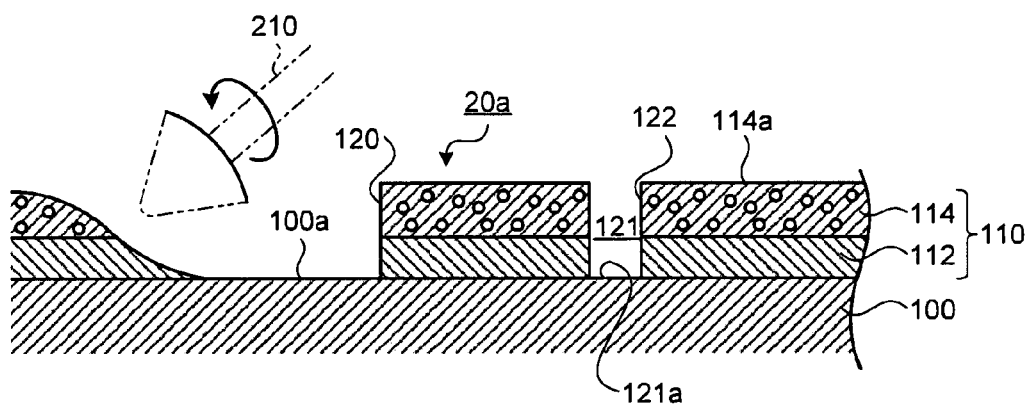
FIG. 5C is a schematic for explaining a process in each step of collecting a specimen according to the first embodiment, in which a state of the blade when a grinder is cutting an area around the cylindrical incision is shown.
Figure 5D:
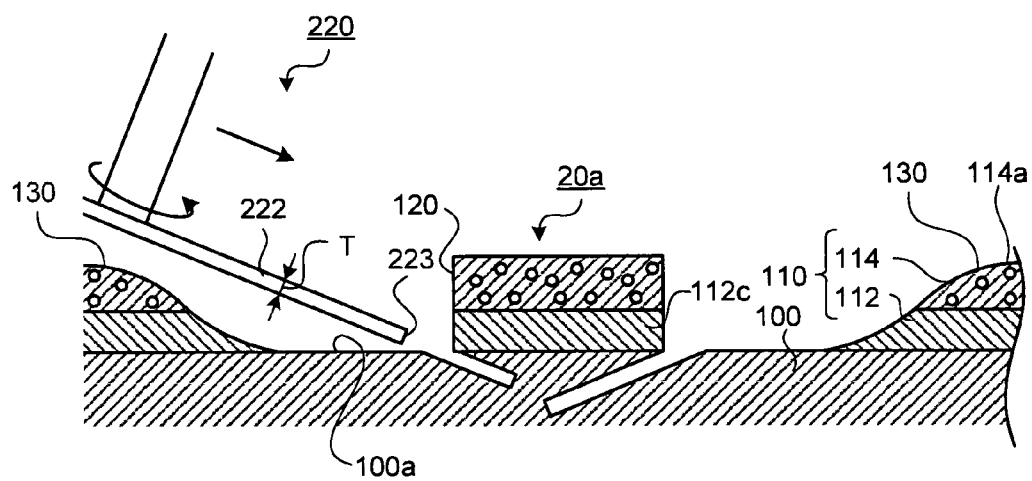
FIG. 5D is a schematic for explaining a process in each step of collecting a specimen according to the first embodiment, in which a state of the blade when a rotating cutter having a disc-shaped cutting blade is cutting the base material under the specimen is shown.
Figure 5E:
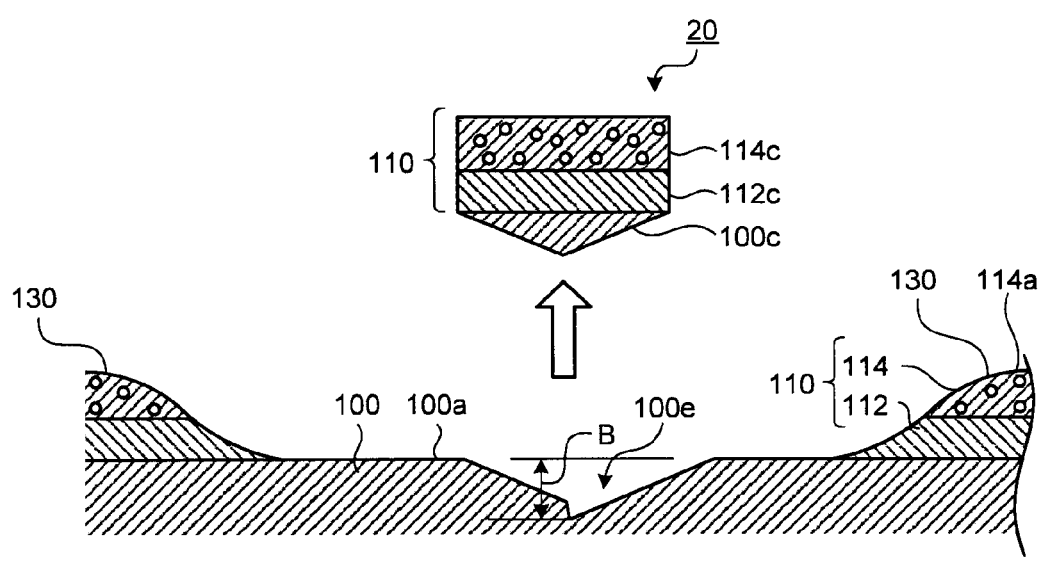
FIG. 5E is a schematic for explaining a process in each step of collecting a specimen according to the first embodiment, in which a state of the blade when the specimen is cut away from the base material is shown.
Figure 6:
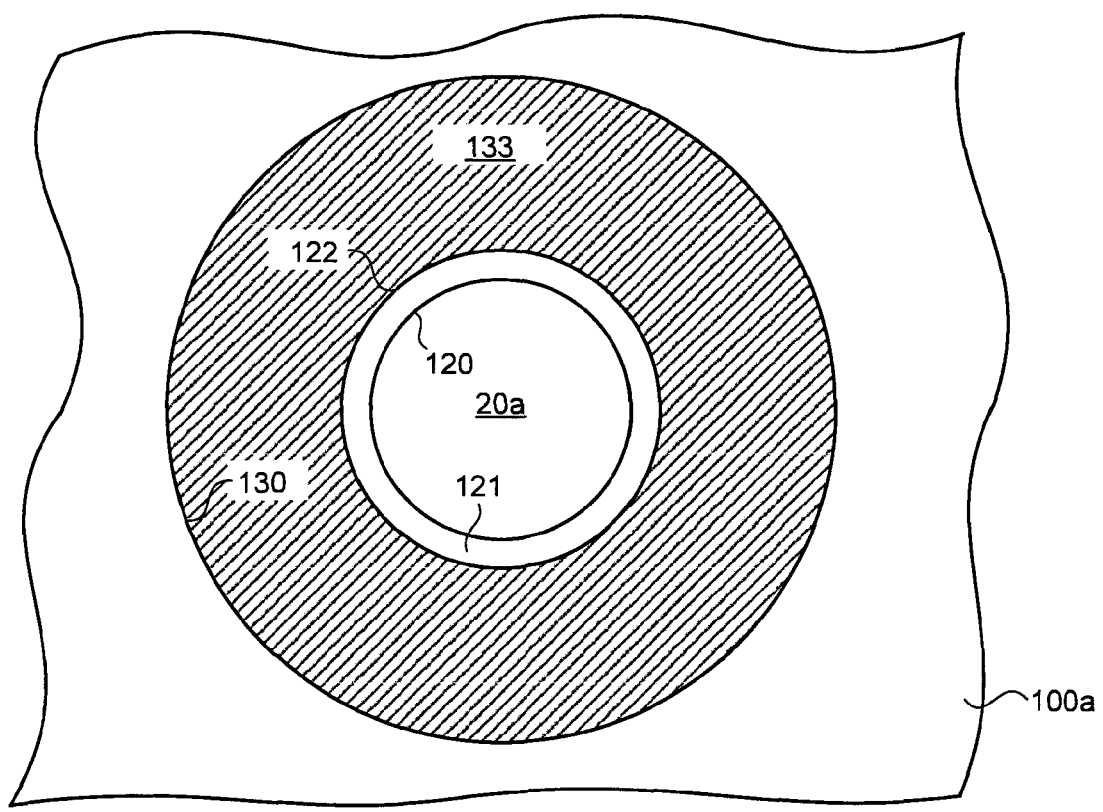
FIG. 6 is a top view of the thermal barrier coat while the specimen is collected according to the first embodiment.

FIG. 5A depicts a state of the blade before being processed. FIG. 5B depicts a state of the blade when the cylindrical incision is formed in the thermal barrier coat. FIG. 5C depicts a state of the blade when a grinder is cutting an area around the cylindrical incision. FIG. 5D depicts a state of the blade when a rotating cutter having a disc-shaped cutting blade is cutting the base material 100 under the specimen. FIG. 5E depicts a state of the blade when the specimen is separated from the base material.

As shown in FIG. 4, an ultrasonic cutter 200 used in the present embodiment cuts a processing object member by minutely vibrating a cutting blade 202. The cutting blade 202 of the ultrasonic cutter 200 has a cylindrical shape, and a diameter D thereof is 3 millimeters to 5 millimeters. With the ultrasonic cutter 200, the cylindrical incision can be formed on the thermal barrier coat 110 by pushing the cutting blade 202 against the thermal barrier coat 110. With the ultrasonic cutter 200, an amount of the cutting blade fed, that is, a distance (indicated by an arrow A shown in FIG. 4) the cutting blade 202 moved in the direction from the top coat 114 to the base material 100, can be monitored.

As shown in FIG. 5A, cutting of the top coat 114 is started by vertically contacting the cylindrical cutting blade 202 onto the thermal barrier coat 110 from above and by vibrating the cutting blade 202. While cutting the top coat 114 and the bond coat 112, the cutting blade 202 is fed as much as the width of the thermal barrier coat 110 toward the base material 100 as indicated by the arrow A.

Vibrating frequency of the cutting blade 202 of the ultrasonic cutter 200 is 1 kilohertz to 50 kilohertz. As the vibrating frequency increases, a cutting speed of the cutting blade 202, that is, a feeding speed thereof, can be higher. With the vibrating frequency equal to or larger than 50 kilohertz, however, the cutting speed is too high and the top coat 114 may be damaged. On the other hand, with the vibrating frequency equal to or smaller than 1 kilohertz, the cutting speed is equal to or lower than one hundredth of a standard condition described later. Thus, the cutting speed is significantly low. In the standard condition in the present embodiment, the vibrating frequency of the cutting blade 202 is set to be 25 kilohertz and the feeding speed of the cutting blade 202 is set to be 0.5 mm/min.

Carborundum (SiC) is used as abrasive grain of the ultrasonic cutter 200. Abrasive grain having a grain size of #240 to #1000, that is, abrasive grain having a diameter of about 60 micrometers to 16 micrometers, is used in the ultrasonic cutter 200. In the standard condition in the present embodiment, a grain size is set to be #400, that is, a diameter of the abrasive grain is set to be about 30 micrometers. If a grain size is smaller than #240, that is, if a diameter of the abrasive grain is large, the cutting speed can be increased. However, with the speed, the cutting surface is more likely to be damaged. On the other hand, if a grain size is larger than #1000, that is, if a diameter of the abrasive grain is small, the cutting speed is significantly low.

As shown in FIG. 5B, the thermal barrier coat 110 is cut until the cutting blade 202 of the ultrasonic cutter 200 comes in contact with a base material surface 100a that is a boundary between the base material 100 and the thermal barrier coat 110 (incision forming step). Thus, as shown in FIG. 6, a cylindrical incision 121 can be formed on the thermal barrier coat 110. In the thermal barrier coat 110, an area surrounded by the cylindrical incision 121 becomes a specimen 20 described later in detail. In other words, an inner edge 120 of the incision 121 is the edge of the specimen 20.

As shown in FIG. 5C, the portion of the thermal barrier coat 110 located outside of the incision 121 is removed by using a tool such as a grinder so that a rotating cutter 220 having a disc-shaped cutting blade 222 (cutting unit) can be inserted to the base material 100 thereat at a later step. More specifically, as shown in FIG. 6, the thermal barrier coat 110 neighboring the outer edge 122 of the incision 121 is cut from the outer edge 122 to an edge 130 that is located at a predetermined distance away from the edge 122 along the surface 100a of the base material 100. Thus, the incision 121 is expanded (incision expanding step). The edge 130 is continual to the surface 114a of the top coat 114 before the thermal barrier coat 110 is cut. That is, the thermal barrier coat 110 is cut into a plate between the outer edge 122 of the incision 121 and the edge 130 located a predetermined distance away from the edge 122 so that as the distance from the outer edge 122 toward the edge 130 increases, the distance from the surface 100a of the base material 100 toward the surface 114a of the top coat 114 decreases. Accordingly, an area 133 in the thermal barrier coat 110 neighboring the outer edge 122 of the incision 121 is cut away as described above, the incision 121 is expanded outwardly and formed into a plate.

As shown in FIG. 5D, the rotating cutter 220 having the cutting blade 222 (cutting unit) that is very thin and disc-shaped cuts a part 20a that becomes the specimen 20 later. The section of the part 20a cut by the rotating cutter 220 is situated closer to the base material 100 than the bond coat 112.

The rotating cutter 220 has the cylindrical cutting blade 222, which is a disk provided with diamond abrasive grain by electrodepositing. The rotating cutter 220 can cut an area of a processing object member contacting the cutting blade 222 by rotating the disc-shaped cutting blade 222. The cutting blade 222 having a thickness T of 0.05 millimeter to 0.4 millimeter is used in the rotating cutter 220. In the present embodiment, the cutting blade having the cutting blade width T of 0.2 millimeter is used in the rotating cutter 220. If the cutting blade 222 having a cutting blade width smaller than 0.05 millimeter is used in the rotating cutter 220, the cutting blade 222 is bent while cutting the thermal barrier coat 110. On the other hand, it is not favorable to use the cutting blade 222 having a width that is larger than 0.4 millimeter in the rotating cutter 220 because a "cutting overlap width" becomes larger therewith, and thus, the area of the base material 100 cut becomes large. An external diameter of the disc-shaped cutting blade 222 of the rotating cutter 220 is sufficiently larger than an inner diameter D2 of the cylindrical cutting blade 202 of the ultrasonic cutter 200.

A cutting edge 223 of the rotating cutter 220 is inserted to the part 20a that becomes the specimen 20 so that the bond coat 112 in the part 20a is not cut away. To minimize an amount of the base material 100 located under the bond coat 112 that is cut away, the rotating cutter 220 is inserted to the part 20a so that an angle between a disc surface 222a and the surface 100a of the base material 100 is as small as possible.

By using the rotating cutter 220, the base material 100 is cut inwardly from the part 20a that later becomes the specimen 20 all around the inner edge 120 of the cylindrical incision 121. Thus, as shown in FIG. 5E, the specimen 20 is cut away from one of the blades 10 (11) (specimen cutting away step). Thus, in the present embodiment, the specimen can be collected that corresponds to an inner diameter of the cylindrical cutting blade 202 of the ultrasonic cutter 200. The specimen 20 thus obtained is used for evaluating the deterioration of the thermal barrier coat 110. Here, the "inwardly" means in the direction from the incision 121 toward the center of the part 20a that later becomes the specimen, that is, the direction radially inward the cylindrical incision 121.

When the specimen 20 is collected, a part 110c of the base material 100 is also cut away along with the top coat 114 and the bond coat 112 of the specimen 20. Thus, a depression 110e that is a trace of the part 110c of the base material 100 that is cut away from the base material 100 is formed on the base material 100. If a depth B of a depression 100e from the surface 100a of the base material 100 is about 0.5 millimeter, by forming the thermal barrier coat 110 again at the depression 100e, the blade 10 (11) having the depression 100e can be used again as the blade 10 (11) of the turbine 5 of the gas turbine 1.

As described above, the present embodiment includes the step of forming the cylindrical incision 121 from the surface 114a of the thermal barrier coat 110 to the surface of the base material 100 with the ultrasonic cutter 200 having the cylindrical cutting blade 202 and the step of cutting away the specimen 20 by cutting the thermal barrier coat 110 inwardly from the cylindrical incision 121 with the rotating cutter 220 having the disc-shaped cutting blade 222. Thus, in collecting the specimen 20, the specimen 20 including the thermal barrier coat 110 can be obtained while minimizing the impact force applied to the thermal barrier coat 110. Thus, optical observation of the oxide scale layer 112s can be accurately performed, such as measuring a thickness of an oxide scale layer 112a formed on the bond coat 112 of the thermal barrier coat 110 provided on the blade 10 (11). As a result, in the gas turbine 1, deterioration of the thermal barrier coat 110 can be evaluated without replacing the blade 10 (11) of the turbine 5.

In the present embodiment, the incision 121 is expanded by cutting the thermal barrier coat 110 situated outside of the incision 121 all around the incision 121 after the incision 121 is formed by using the ultrasonic cutter 200. Then, the thermal barrier coat 110 is cut by the rotating cutter 220 inwardly from the incision 121. Because the rotating cutter 220 is inserted to the incision 121 after the incision is expanded outwardly, the rotating cutter 220 can be inserted to the thermal barrier coat 110 so that an angle between the rotating cutter 220 and the surface of the base material 100 is as small as possible even if the difference between the inner diameter D2 and the external diameter D1 provided by the ultrasonic cutter 200 is small and a distance between the inner edge 120 and the outer edge 122 of the incision 121 is small. As a result, an amount of the base material 100 cut away along with the thermal barrier coat 110 in the specimen 20 can be made as small as possible, and the depression 100e formed on the base material 100 after the specimen 20 is cut away from the thermal barrier coat 110 can be as shallow as possible.

In the present embodiment, only one cylindrical incision 121 that is round shaped is formed with the ultrasonic cutter 200. However, examples of the incision 121 are not limited thereto. For example, as shown in FIG. 7, a plurality of incisions 121c and 121f can preferably be formed so that the incisions 121c and 121f partially overlap. By overlapping the incisions 121c and 121f, a ratio between the total surface of the specimens that can be obtained (20c, 20e, and 20f) and a surface of a region 135 that is outwardly expanded from the incisions 121c and the 121f can be smaller than when only one incision 121 is formed. Thus, the specimens 20c, 20e, and 20f can be obtained while minimizing the step of outwardly expanding the incision 121, which is cumbersome compared to other steps.

Second Embodiment

Figure 8A:
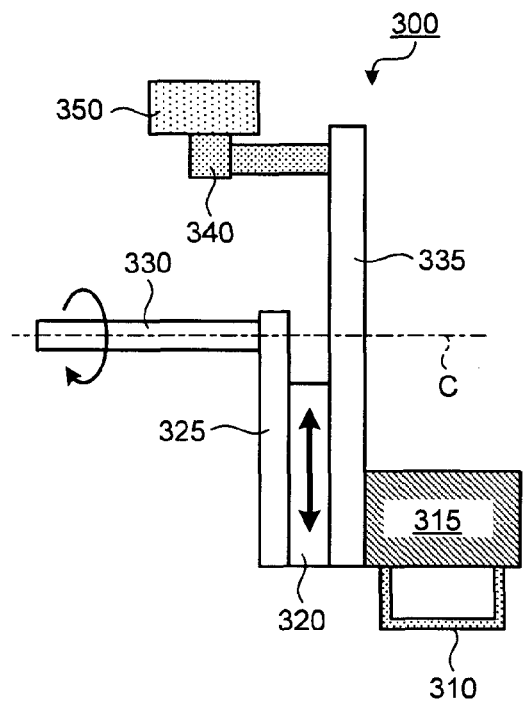
FIG. 8A is a front view of a discharge wire cutting device according to a second embodiment of the present invention.
Figure 8B:
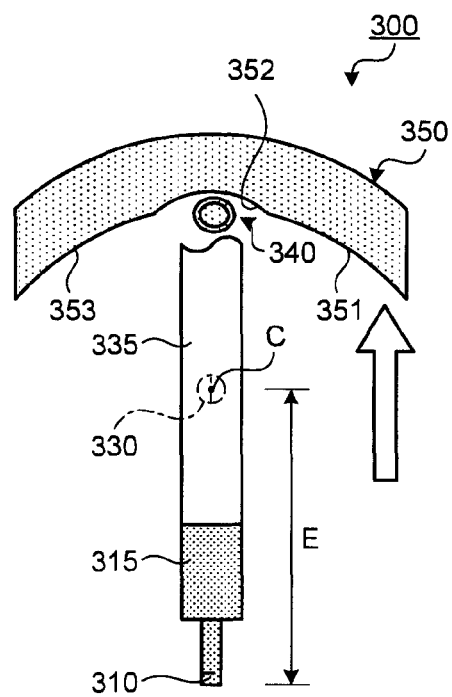
FIG. 8B is a side view of the discharge wire cutting device according to the second embodiment.
Figure 9A:
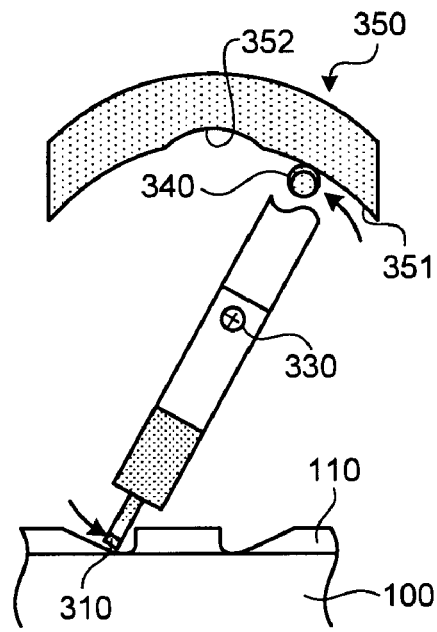
FIG. 9A is a schematic for explaining an operation performed by the discharge wire cutting device according to the second embodiment, in which an electrode of the discharge wire cutting device entering into the incision formed in the thermal barrier coat is shown.
Figure 9B:
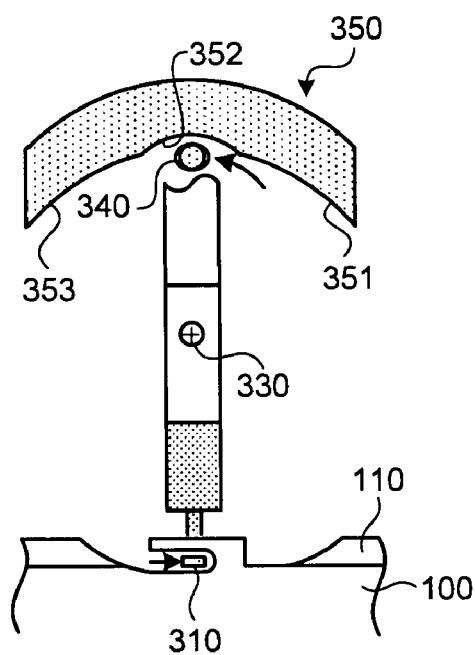
FIG. 9B is a schematic for explaining an operation performed by the discharge wire cutting device according to the second embodiment, in which the electrode moving along the surface of the base material while cutting the specimen is shown.
Figure 9C:
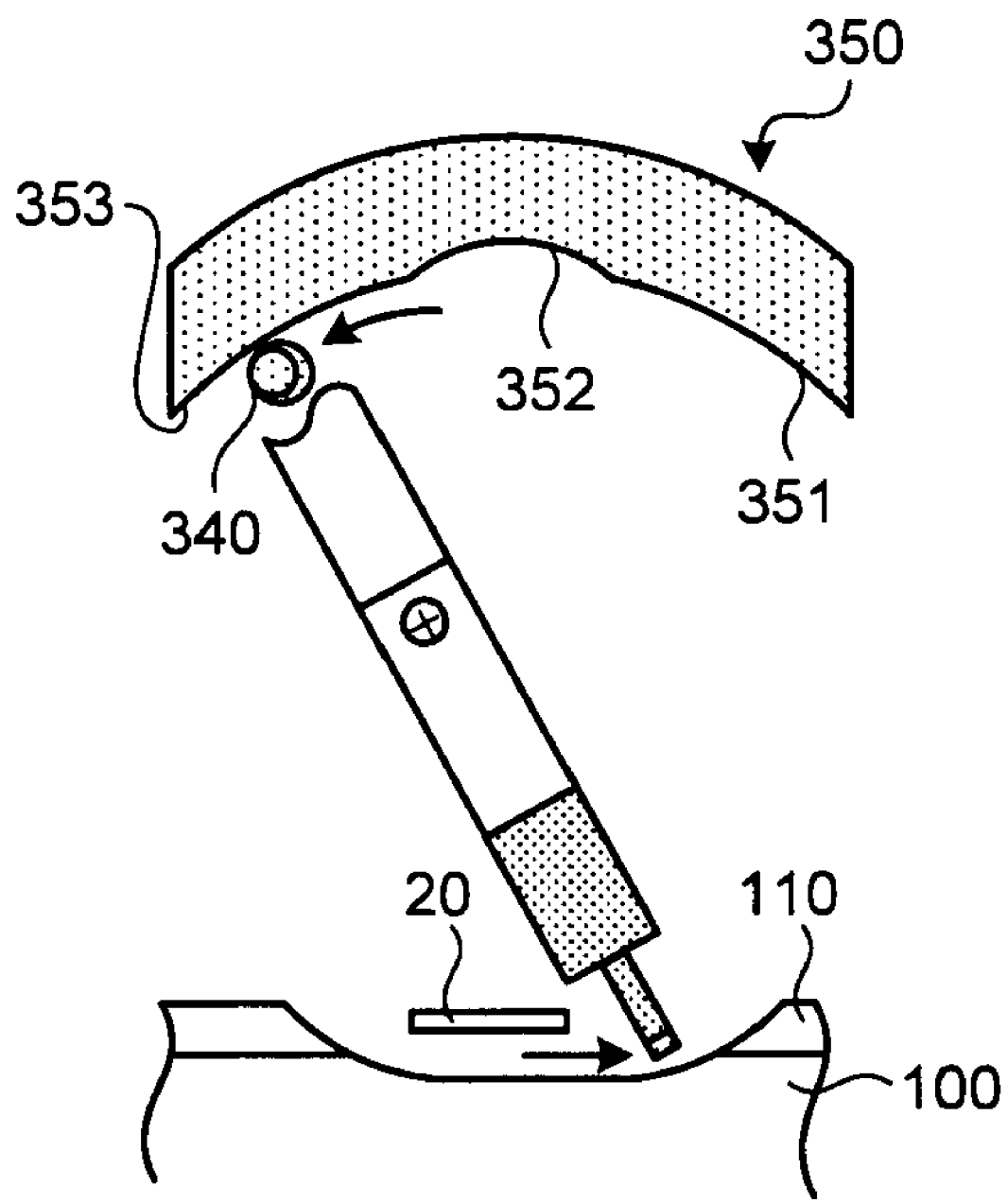
FIG. 9C is a schematic for explaining an operation performed by the discharge wire cutting device according to the second embodiment, in which the electrode exiting the incision after the cutting of the specimen is completed is shown.

A specimen collecting method of a thermal barrier coat according to a second embodiment of the present invention is described below in greater detail with reference to FIGS. 5B, 5C, and 8A to 9C. FIG. 8A is a front view of a discharge wire cutting device. FIG. 8B is a side view of the discharge wire cutting device. FIGS. 9A to 9C are schematics for explaining operation performed by the discharge wire cutting device. FIG. 9A depicts a state where when an electrode of the discharge wire cutting device is entering the incision formed in the thermal barrier coat. FIG. 9B depicts a state where the electrode moves along the surface of the base material, while cutting the thermal barrier coat by utilizing electric discharge. FIG. 9C depicts a state where the electrode is exiting the incision after finishing cutting the specimen. The present embodiment is different from the first embodiment in that the discharge wire cutting device is used in place of the rotating cutter to cut the specimen of the thermal barrier coat. The present embodiment is described below in greater detail. Configurations of the gas turbine, the blades, and the thermal barrier coat are similar to that of the first embodiment. Accordingly, the gas turbine, the blades, and the thermal barrier coat are given the identical reference characteristics and detail descriptions thereof are omitted.

As shown in FIG. 8A, a discharge wire cutting device 300 includes: an electrode 310 having a U-shaped wire and can cut metal with electrical discharge; and an electrode holder 315 that holds the electrode 310.

Electrical power is supplied from a power supply (not shown) to the electrode 310. The electrode 310 can cut the blade 10 (11) by generating electrical discharge between the blade 10 (11), that is a metal member and a processing object member, and the electrode 310

The discharge wire cutting device 300 includes a rotating shaft 330 that rotates the electrode holder 315, a sliding mechanism 320 connected to the rotating shaft 330 via a stay 325, and the stay 325 that transmits, to the electrode holder 315, rotating movement of the rotating shaft 330 that transmits movement of a roller 340 to the electrode holder 315. The rotating shaft 330 is connected to a motor (not shown), and is rotated about a shaft center C of the rotating shaft 330. The rotating movement of the rotating shaft 330 is transmitted from the stay 325 to the electrode holder 315 via the later described sliding mechanism 320. Thus, the electrode 310 can be rotated in the circumferential direction of the rotating shaft 330.

The discharge wire cutting device 300 further includes: the sliding mechanism 320 that enables the electrode 310 and the electrode holder 315 to slide in the radial direction of the rotating shaft 330; a guiding slide 350 on which outline surfaces (profile surfaces 351, 352, and 353) are provided that defines movement of the electrode 310 in the radial direction; the roller 340 that moves along the outline surfaces 351, 352, and 353 of the guiding slide 350; a rod that transmits movement of the roller 340 in the radial direction of the rotating shaft 330 to the electrode holder 315 and the electrode 310.

The roller 340 is rotatably supported with respect to a rod 335, and moves along the outline surfaces (351, 352, and 353) of the guiding slide 350. The rod 335 biases the roller 340 with a spring (not shown) in the radial direction of the rotating shaft 330 toward the outline surfaces (351, 352, and 353) of the guiding slide 350. Thus, the roller 340 can move along the outline surfaces (351, 352, and 353) of the guiding slide 350, and the rod 335 is driven in the radial direction of the rotating shaft 330 according to the outline of the guiding slide 350. The electrode holder 315 is connected to the rod 335, and is connected to the rotating shaft 330 via the sliding mechanism 320. Thus, the rotating movement of the rotating shaft 330 and the sliding movement of the rod 335 in the radial direction of the rotating shaft 330 that is defined by the outline surfaces (351, 352, and 353) of the guiding slide 350 are integrated together, and movement thus integrated is transmitted to the electrode holder 315 and the electrode 310.

In the discharge wire cutting device 300 that is configured as described above, as shown in FIG. 8B, the electrode 310 slides in the radial direction of the rotating shaft 330 by a distance that corresponds to a difference made on the cross-sectional shape of the outline surface (351, 352, and 353) of the guiding slide 350 from the shape of the circle of which the center is the shaft center C of the rotating shaft 330. That is, in the discharge wire cutting device 300, by setting the cross-sectional shape of the outline surfaces (351, 352, and 353) of the guiding slide 350, a distance E between the shaft center C of the rotating shaft 330 and the electrode 310 can be adjusted to be a desired value corresponding to a rotating angle position of the electrode 310.

In the specimen collecting method of the thermal barrier coat according to the present embodiment, similarly to the first embodiment, as shown in FIG. 5B, the cylindrical incision 121 is formed from the thermal barrier coat 110 to the base material 100 with the ultrasonic cutter 200 having the cylindrical cutting blade 202 (incision forming step). As shown in FIG. 5C, the incision 121 is outwardly expanded by cutting away the thermal barrier coat 110 situated radially outward of the outer edge of the incision 121 (incision expanding step).

The blade 10 (11) on which the incision 121 is formed is fitted to the discharge wire cutting device 300 as shown in FIG. 9A. The rotating shaft 330 is rotated by controlling the motor (not shown) and an electric voltage is applied to the electrode 310, and thus, electrical discharge is generated. The roller 340 moves along a first surface 351 of the outline surfaces (351, 352, and 353) of the guiding slide 350, and thus, the electrode 310 moves in a rotating manner in the circumferential direction of the rotating shaft 330. As a result, the electrode 310 enters the incision 121.

Then, the roller 340 moves along a second surface 352 that is situated in the middle of the outline surfaces (351, 352, and 353), as shown in FIG. 9B. In the second surface 352, the depression 100e is formed so that the electrode 310 slides more toward the side of the guiding slide 350 in the radial direction of the rotating shaft 330 than in the first surface 351. The shape of the second surface 352 is configured so that the electrode 310, that is provided on the other side of the roller 340 with the rotating shaft 330 in the center between each other, moves along the surface 100a of the base material 100 and the thermal barrier coat 110 in parallel thereto when the roller 340 moves along the second surface 352. With such configuration, the electrode 310 moves along the surface 100a, and the electrode 310 cuts along the surface 100a of the base material 100 by generating electrical discharge between the electrode 310 and the thermal barrier coat 110 and the base material 100 (specimen cutting away step).

When the roller 340 moves from the second surface 352 to a third surface 353, the specimen 20 is cut away from the blade 10 (11), and then, the electrode 310 gets out of the incision 121. Thus, the discharge wire cutting device 300 can cut away the specimen 20 of the thermal barrier coat 110 from the surface of the blade 10 (11).

As described above, in the specimen collecting method of the thermal barrier coat 110 according to the present embodiment, the discharge wire cutting device 300 in which the distance E between the rotating shaft 330 and the electrode 310 can be adjusted to a desired value corresponding to the rotating angle position of the electrode 310, is used to cut the thermal barrier coat 110 inwardly from the cylindrical incision 121 to cut away the specimen 20. Therefore, an amount of the base material 100 contained in the specimen 20 of the thermal barrier coat 110 can be minimized.

In the present embodiment, the discharge wire cutting device 300 includes the guiding slide 350, the roller 340 that moves along the outline surfaces (351, 352, and 353) of the guiding slide 350, and the roller 340 that rotatably instructs the roller 340 and that is connected to the electrode holder 315. However, the configuration of the discharge wire cutting device 300 according to the present invention is not limited thereto. The discharge wire cutting device 300 may take any configurations as long as the distance E between the rotating shaft 330 and the electrode 310 can be adjusted to desired value corresponding to a rotating angle position of the electrode 310. For example, the discharge wire cutting device 300 according to the present invention may be configured without the guiding slide 350, the roller 340, and the rod 335, and an actuator that is extendable with a control device can be provided in place of the sliding mechanism 320 that holds the electrode holder 315.

Third Embodiment

In a third embodiment of the present invention, a method is described that estimates a "metal temperature", i.e., a temperature of the base material, from the specimen of the thermal barrier coat obtained with the collecting method of the specimen according to the first or the second embodiment. The present embodiment is described below in detail. Here, configurations of the gas turbine, the blades, and the thermal barrier coat are similar to that of the first embodiment. Accordingly, the gas turbine, the blades, and the thermal barrier coat are given the identical reference characteristics and the detail descriptions thereof are omitted.

In a metal temperature estimating method according to the present embodiment of estimating a metal temperature of the blade 10 (11) in which the bond coat 112 and the top coat 114 are sequentially formed on the base material 100, relationships between a thickness, a temperature, and a time of the oxide scale layer 112s are obtained in advance from a test piece having the same composition as the blade 10 (11). Then, utilizing the relationships, a metal temperature of the blade 10 (11) is estimated based on a thickness of the oxide scale layer 112s of the specimen 20 obtained from the gas turbine 1. Thus, while minimizing the damage applied to the base material 100 of the blade 10 (11), the timing of the deterioration of the blade 10 (11) such as separation of the top coat 114 can be predicted, and a remnant service life of the blade 10 (11) can be evaluated. With the method, the deterioration of the blade can be evaluated at low cost because the blade needs not to be replaced.

In a metal temperature estimating method according to the present embodiment of estimating a metal temperature of the blade 10 (11) in which the bond coat 112 and the top coat 114 are sequentially formed on the base material 100, relationships between a disappearing depth, a temperature, and a time of a deposition substance formed on the surface side of the blade 10 (11) is obtained in advance from a test piece having the same composition as the blade 10 (11). Then, utilizing the relationships, a metal temperature of the blade 10 (11) is estimated based on a disappearing depth of a deposition substance formed on the specimen 20 obtained from the gas turbine 1. Also with the method, the timing of the deterioration of the blade 10 (11) such as separation of the top coat 114 can be predicted, and a remnant service life of the blade 10 (11) can be evaluated.

In a metal temperature estimating method according to the present embodiment of estimating a metal temperature of the blade 10 (11) in which the bond coat 112 is formed on the base material 100, a relationship between a thickness and a temperature of a diffuse layer formed on the surface of the base material 100, and time is obtained in advance from a test piece having the same composition as the blade 10 (11). Then, utilizing the relationships, a metal temperature of a component that is at a high temperature is estimated based on a thickness of a diffuse layer of the specimen 20 obtained from the gas turbine 1. Also with the method, the timing of the deterioration of the blade 10 (11) such as separation of the top coat 114 can be predicted, and a remnant service life of the blade 10 (11) can be evaluated.

In a metal temperature estimating method according to the present embodiment of estimating a metal temperature of the blade 10 (11) in which the bond coat 112 is formed on the base material 100, a relationship between a disappearing depth of a deposition substance formed on the blade 10 (11) on the side of the base material 100, a temperature of the base material 100, and time is obtained in advance from a test piece having the same composition as the blade 10 (11). Then, utilizing the relationship, a metal temperature of a component that is at a high temperature is estimated based on a disappearing depth of a deposition substance formed on the specimen 20 obtained from the gas turbine 1. Also with the method, the timing of the deterioration of the blade 10 (11) such as separation of the top coat 114 can be predicted, and a remnant service life of the blade 10 (11) can be evaluated.

Detailed information about the metal temperature estimating method according to the present embodiment is described in detail in the paragraphs [0001] to [0028] in Japanese Patent No. 3794939 by the present applicant. The present embodiment includes drawings described in relation to the above paragraphs.

Fourth Embodiment

In a temperature estimating method of the blade 10 (11) according to a fourth embodiment of the present invention, a temperature of the top coat 114 of the blade 10 (11) is estimated based on the specimen 20 of the thermal barrier coat 110 obtained according to a collecting method of the specimen 20 according to the first or the second embodiment. The present embodiment is described below in detail. Here, configurations of the gas turbine, the blade 10 (11), and the thermal barrier coat 110 are similar to the first embodiment. Accordingly, the gas turbine, the blade, and the thermal barrier coat are given the identical reference characteristics and the detail descriptions thereof are omitted.

In a temperature estimating method of the blade 10 (11) according to the present embodiment, a temperature of the blade 10 (11) in which the top coat 114 that is a ceramic layer is formed on the base material 100 is estimated. An amount of monoclinic crystal formed on the top coat 114 is measured by using X-ray crystallography, and then, based on the amount of the monoclinic crystal, a surface temperature of the top coat 114 is estimated. Thus, the surface temperature of the top coat 114 can be nondestructively estimated. Accordingly, the timing of the deterioration of the blade 10 (11) such as separation of the top coat 114 can be predicted, and a remnant service life of the blade 10 (11) can be evaluated. With the method, the deterioration of the blade can be evaluated at low cost because the blade needs not to be replaced.

In a temperature estimating method of the blade 10 (11) in which the top coat 114 is formed on the base material 100, an surface rate of a film shaped defect is obtained by performing image processing of a microstructure of the cross-section, along the direction of the depth of the top coat 114, of the obtained specimen 20. Based on the surface rate, a surface temperature of the top coat 114 is estimated. Also with the method, the timing of the deterioration of the blade 10 (11) such as separation of the top coat 114 can be predicted, and a remnant service life of the blade 10 (11) can be evaluated.

In a temperature estimating method of the blade 10 (11) in which the top coat 114 is formed on the base material 100, a hardness of the cross-section of the top coat 114 along the direction of depth of the top coat 114 is obtained. Based on the hardness, a surface temperature of the top coat 114 is estimated. Also with the method, the timing of the deterioration of the blade 10 (11) such as separation of the top coat 114 can be predicted, and a remnant service life of the blade 10 (11) can be evaluated.

Detailed information about the metal temperature estimating method according to the present embodiment is described in detail in the paragraphs [0001] to [0038] in Japanese Patent No. 3519703 by the present applicant. The present embodiment includes the paragraphs.

In the embodiment described above, the bond coat 112 that is an oxidation resistant layer and the top coat 114 that is a ceramic layer are sequentially provided on the base material 100 as the thermal barrier coat 110, and the specimen 20 is constituted mainly of the bond coat 112 and the top coat 114. However, the configurations of the thermal barrier coat 110 and the specimen 20 are not limited thereto. For example, an oxidation resistant layer may separately be provided between the bond coat provided on the base material and the top coat that constitutes the surface of the blade.

INDUSTRIAL APPLICABILITY

As described above, the method of collecting a specimen according to the present embodiment is useful in evaluating the deterioration of a thermal barrier coat provided on a blade of a turbine, and more particularly, for evaluating the deterioration of a blade of an industrial gas turbine.

The invention claimed is:
1. A specimen collecting method of collecting a specimen from a member whose surface is provided with a layer, the specimen collecting method comprising:
an incision forming step of forming a cylindrical incision by feeding a cylindrical cutter having a cylindrical cutting blade from the surface in the direction of thickness of the member to perform cutting; and
a specimen cutting away step of cutting away a specimen formed inside the incision by inwardly cutting the member from the cylindrical incision, the specimen collecting method further comprising an incision expanding step of cutting the member so that the incision is outwardly expanded after forming the cylindrical incision by cutting away an area located radially outward of an outer edge of the incision, wherein a rotating cutter having a disc-shaped cutting blade is inserted to the cylindrical incision to cut the member at the specimen cutting away step.
2. The specimen collecting method according to claim 1, wherein
the member is a blade of a gas turbine,
a surface of the blade is formed by providing a layer of a thermal barrier coat on a base material,
the cylindrical cutter is fed until the cylindrical cutter comes in contact with the base material at the incision forming step, and
the rotating cutter cuts the base material at the specimen cutting away step.

3. The specimen collecting method according to claim 1, wherein a plurality of incisions is formed so that the incisions partially overlap at the incision forming step.

4. A temperature estimating method of a blade in which a bond coat and a top coat are sequentially formed on a base material by using a specimen, which is obtained by the specimen collecting method comprising steps of an incision forming step of forming a cylindrical incision by feeding a cylindrical cutter having a cylindrical cutting blade from the surface in the direction of thickness of the member to perform cutting, wherein a plurality of incisions is formed so that the incisions partially overlap at the incision forming step; an incision expanding step of cutting the member so that the incision is outwardly expanded after forming the cylindrical incision, and a specimen cutting away step of cutting away a specimen formed inside the incision by inwardly cutting the member from the cylindrical incision, wherein a rotating cutter having a disc-shaped cutting blade is inserted to the cylindrical incision to cut the member at the specimen cutting away step, wherein
 a relationship between a thickness and a temperature of an oxide scale layer of the blade, and time is obtained based on a test piece having a same composition as the blade, and then, by utilizing the relationship, a metal temperature of the blade is estimated based on the thickness of the oxide scale layer of the specimen obtained from the gas turbine.

5. A temperature estimating method of a blade formed with a top coat that is a ceramic layer on a base material by using a specimen, which is obtained by the specimen collecting method comprising steps of an incision forming step of forming a cylindrical incision by feeding a cylindrical cutter having a cylindrical cutting blade from the surface in the direction of thickness of the member to perform cutting, wherein a plurality of incisions is formed so that the incisions partially overlap at the incision forming step; an incision expanding step of cutting the member so that the incision is outwardly expanded after forming the cylindrical incision, and a specimen cutting away step of cutting away a specimen formed inside the incision by inwardly cutting the member from the cylindrical incision, wherein a rotating cutter having a disc-shaped cutting blade is inserted to the cylindrical incision to cut the member at the specimen cutting away step, wherein
 an amount of a monoclinic crystal formed on the top coat of the obtained specimen is measured by X-ray diffraction method, and a surface temperature of the top coat is estimated based on the amount of the monoclinic crystal.

* * * * *